United States Patent
Lee et al.

(10) Patent No.: US 10,386,533 B2
(45) Date of Patent: *Aug. 20, 2019

(54) DOWNHOLE TOOL APPARATUS, SYSTEM, AND METHODS

(71) Applicant: Halliburton Energy Services, Inc., Houston, TX (US)

(72) Inventors: Dongwon Lee, Kingwood, TX (US); Weijun Guo, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 65 days.

This patent is subject to a terminal disclaimer.

(21) Appl. No.: 15/534,402

(22) PCT Filed: Mar. 26, 2015

(86) PCT No.: PCT/US2015/022748
§ 371 (c)(1),
(2) Date: Jun. 8, 2017

(87) PCT Pub. No.: WO2016/153524
PCT Pub. Date: Sep. 29, 2016

(65) Prior Publication Data
US 2019/0004205 A1    Jan. 3, 2019

(51) Int. Cl.
*G01V 5/08* (2006.01)
*G01V 5/12* (2006.01)
(Continued)

(52) U.S. Cl.
CPC ............ *G01V 5/08* (2013.01); *E21B 47/0005* (2013.01); *E21B 49/08* (2013.01); *G01N 23/203* (2013.01);
(Continued)

(58) Field of Classification Search
CPC . G01V 5/08; G01V 5/12; G01V 5/125; E21B 47/0005; E21B 49/08; G01N 23/203
See application file for complete search history.

(56) References Cited

U.S. PATENT DOCUMENTS 3,281,599 A * 10/1966 Baker .................. E21B 49/005
250/268
3,976,879 A    8/1976 Turcotte
(Continued)

FOREIGN PATENT DOCUMENTS

EP    0159484 A1    10/1985
EP    1522848 A1    4/2005
(Continued)

OTHER PUBLICATIONS

"International Application Serial No. PCT/US2015/022729, International Search Report dated Dec. 18, 2015", 3 pgs.
(Continued)

*Primary Examiner* — David P Porta
*Assistant Examiner* — Jeremy S Valentiner
(74) *Attorney, Agent, or Firm* — Gilliam IP PLLC

(57) ABSTRACT

A downhole tool can include a photon beam source configured to transmit a photon beam into materials lining a wellbore. The materials may comprise fluid, casing, and cement. A photon detector in the tool is configured to count detected photons received at a predetermined angle from the materials. The density of the borehole material may be determined in response to the number of detected photons. Changes in a distribution of a plurality of photon count ratio values may indicate the standoff distance. Additional apparatus, systems, and methods are disclosed.

19 Claims, 10 Drawing Sheets

(51) Int. Cl.
*E21B 47/00* (2012.01)
*E21B 49/08* (2006.01)
*G01N 23/203* (2006.01)
*G21K 1/02* (2006.01)

(52) U.S. Cl.
CPC .............. *G01V 5/12* (2013.01); *G01V 5/125* (2013.01); *G21K 1/02* (2013.01)

(56) References Cited

U.S. PATENT DOCUMENTS

| | | | |
|---|---|---|---|
| 4,297,575 A * | 10/1981 | Smith, Jr. | G01V 5/125 250/265 |
| 4,462,082 A | 7/1984 | Thiele et al. | |
| 4,576,034 A | 3/1986 | Ferree et al. | |
| 4,618,765 A * | 10/1986 | Sonne | G01V 5/125 250/269.3 |
| 5,012,091 A | 4/1991 | Moake | |
| 5,204,529 A | 4/1993 | Diatschenko | |
| 5,486,695 A | 1/1996 | Schultz et al. | |
| 5,659,169 A * | 8/1997 | Mickael | G01V 5/12 250/265 |
| 7,587,936 B2 | 9/2009 | Wei | |
| 8,321,131 B2 | 11/2012 | Case | |
| 2001/0035312 A1 | 11/2001 | Han et al. | |
| 2004/0000401 A1 | 1/2004 | Sale et al. | |
| 2004/0200274 A1* | 10/2004 | Moake | G01V 5/125 73/152.05 |
| 2006/0284066 A1* | 12/2006 | Jacobson | G01V 5/101 250/269.6 |
| 2008/0186805 A1 | 8/2008 | Han | |
| 2010/0076688 A1 | 3/2010 | Moake | |
| 2011/0191027 A1 | 8/2011 | Pfutzner et al. | |
| 2011/0284732 A1 | 11/2011 | Korkin et al. | |
| 2012/0059587 A1 | 3/2012 | Marsh et al. | |
| 2012/0138782 A1 | 6/2012 | Simon et al. | |
| 2012/0192640 A1 | 8/2012 | Minh et al. | |
| 2013/0202090 A1 | 8/2013 | Belcher et al. | |
| 2013/0215715 A1 | 8/2013 | Hollstein et al. | |
| 2013/0261974 A1* | 10/2013 | Stewart | G01V 5/045 702/8 |

FOREIGN PATENT DOCUMENTS

| | | |
|---|---|---|
| EP | 1922571 B1 | 8/2012 |
| WO | 1996012977 | 5/1996 |
| WO | 2016153523 A1 | 9/2016 |
| WO | 2016153566 A1 | 9/2016 |
| WO | 2016153567 A1 | 9/2016 |

OTHER PUBLICATIONS

"International Application Serial No. PCT/US2015/022729, Written Opinion dated Dec. 18, 2015", 10 pgs.
"International Application Serial No. PCT/US2015/022748, International Search Report dated Dec. 24, 2015", 3 pgs.
"International Application Serial No. PCT/US2015/022748, Written Opinion dated Dec. 24, 2015", 6 pgs.
"International Application Serial No. PCT/US2015/063693, International Search Report dated Feb. 3, 2016", 3 pgs.
"International Application Serial No. PCT/US2015/063693, Written Opinion dated Feb. 3, 2016", 4 pgs.
"International Application Serial No. PCT/US2015/063711, International Search Report dated Mar. 15, 2016", 3 pgs.
"International Application Serial No. PCT/US2015/063711, Written Opinion dated Mar. 15, 2016", 9 pgs.
Moake, et al., "Standoff and Caliper Measurements While Drilling Using a New Formation-Evaluation Tool With Three Ultrasonic Transducers", SPE Drilling & Completion, Jun. 1, 1995 00:00:00.0, 104-111.
EP Application Serial No. 15886712.7, Extended European Search Report, dated Nov. 19, 2018, 7 pages.
EP Application Serial No. 15886711.9, Extended European Search Report, dated Oct. 23, 2018, 7 pages.
EP Application Serial No. 15886679.8, Extended European Search Report, dated Nov. 6, 2018, 8 pages.

* cited by examiner

DOWNHOLE TOOL APPARATUS, SYSTEM, AND METHODS

BACKGROUND

Natural resources such as gas, oil, and water residing in a geological formation may be recovered by drilling a wellbore into the formation while circulating a drilling fluid in the wellbore. After terminating the circulation of the drilling fluid, a string of pipe (e.g., casing) is run into the wellbore in order to provide structural support for the wellbore sides. A cement slurry is injected into the annulus between the casing and the geological formation. The hardened cement seals the annulus and supports the string of pipe in the wellbore.

Tools (e.g., acoustic, electromagnetic) may be lowered into the wellbore casing to determine properties of deposits (e.g., fluids, gas) in the geological formation. In order to provide more accurate results for these measurements, it can be useful to know the distance between the tool and the casing, as well as the density of material within the casing.

DETAILED DESCRIPTION

To address the challenges noted above, the inventors have discovered that a photon beam source can be configured to transmit a photon beam into a wellbore, with a photon detector configured to count detected photons. These photons are received at a predetermined angle from materials lining the wellbore and are used to determine a density of a borehole material using Compton backscattering to determine standoff.

Figure 1:
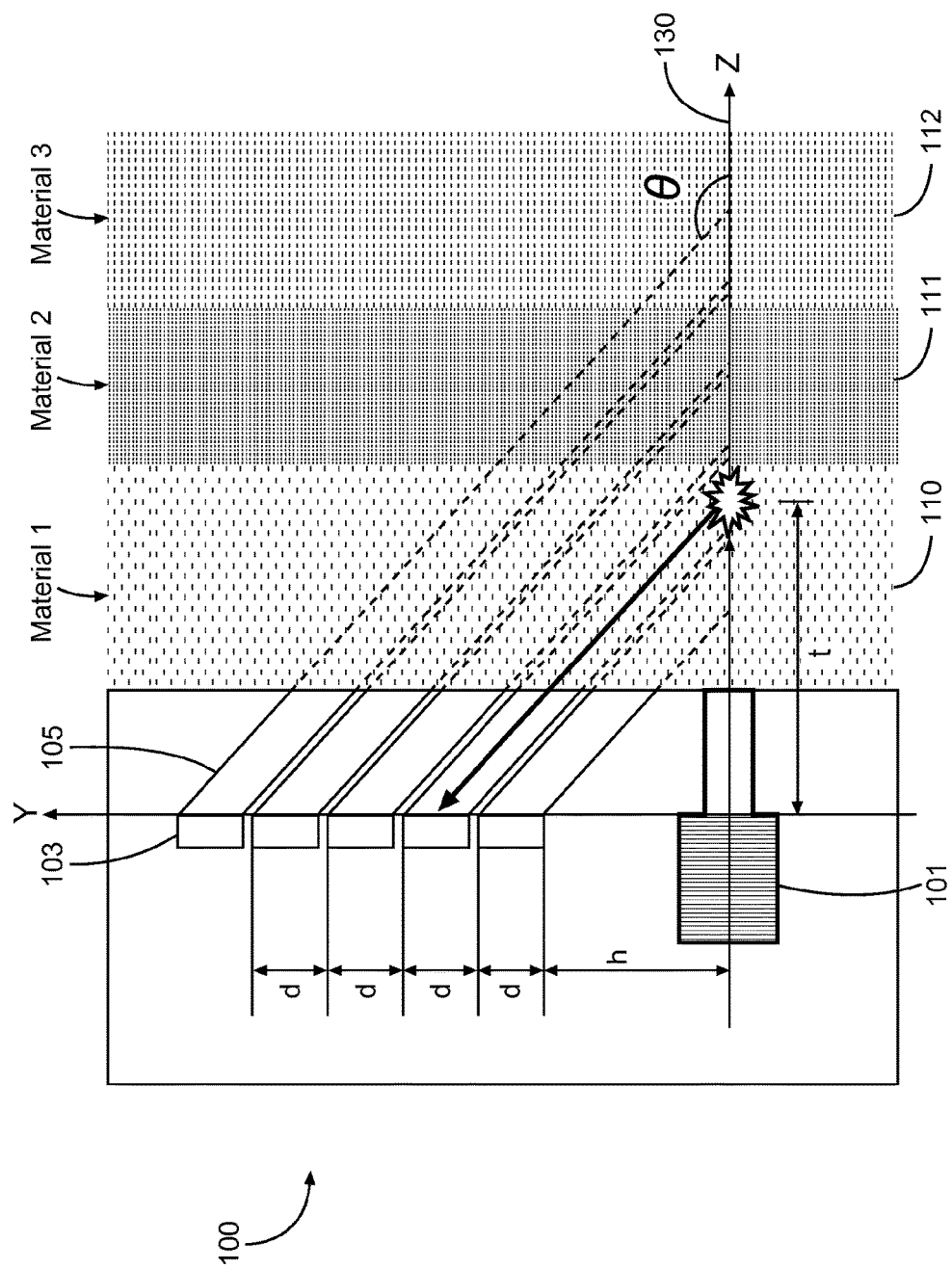
FIG. 1 is a cross-sectional diagram showing an embodiment of a device to determine tool standoff and material density in a borehole.

FIG. 1 is a cross-sectional diagram showing an embodiment of a device to determine tool standoff and material density in a borehole. The device 100 may be incorporated into a downhole tool housing such as a wireline tool housing to be used during a wireline logging operation (see FIG. 7) or a drill string tool housing to be used during a logging while drilling (LWD) operation (see FIG. 8)

The device 100 includes a photon source 101 configured to transmit a photon beam into the surrounding materials 110-112. These materials may include borehole fluid 110, casing 111 (e.g., steel), and cement 112. Other embodiments may have different materials. The photon source 101 may transmit the photon beam substantially perpendicular (i.e., at an included angle of substantially 90°) to the wellbore sides.

The photon source 101 may be any photon source that emits photons at one or more energies or over a broad range of energies. Examples of a photon source 101 include a chemical source (e.g., CS-137), a gamma-ray source, a neutron source, or an electron source (e.g., x-ray tube). A collimated or focused beam of photon flux is used to define the volume of investigation.

The reaction of the photons with the materials 110-112 scatters the photons back to a detector 103. In order to reduce detection to those photons exiting the materials 110-112 at a selected angle $\theta$, a slant-hole collimator 105 is located in front of the detector 103. Thus only those photons traveling in a parallel direction with the collimator 105 may enter the collimator 105 and reach the detector 103. The collimator geometry is designed to accept the photons with single Compton backscattering at a fixed angle, while rejecting photons that have gone through multiple Compton scatterings. The slant-hole collimator design provides one-dimensional (1-D) radial spectrum of the backscattered photons and rotation of the whole housing (e.g., in a wireline or drillstring tool) provides circumferential scans to create a two-dimensional (2-D) tomographic image of the borehole. The collimator 105 may be coupled to the detector 103 in a way that light transmission is enhanced between the collimator 105 and the detector 103.

Figure 2:
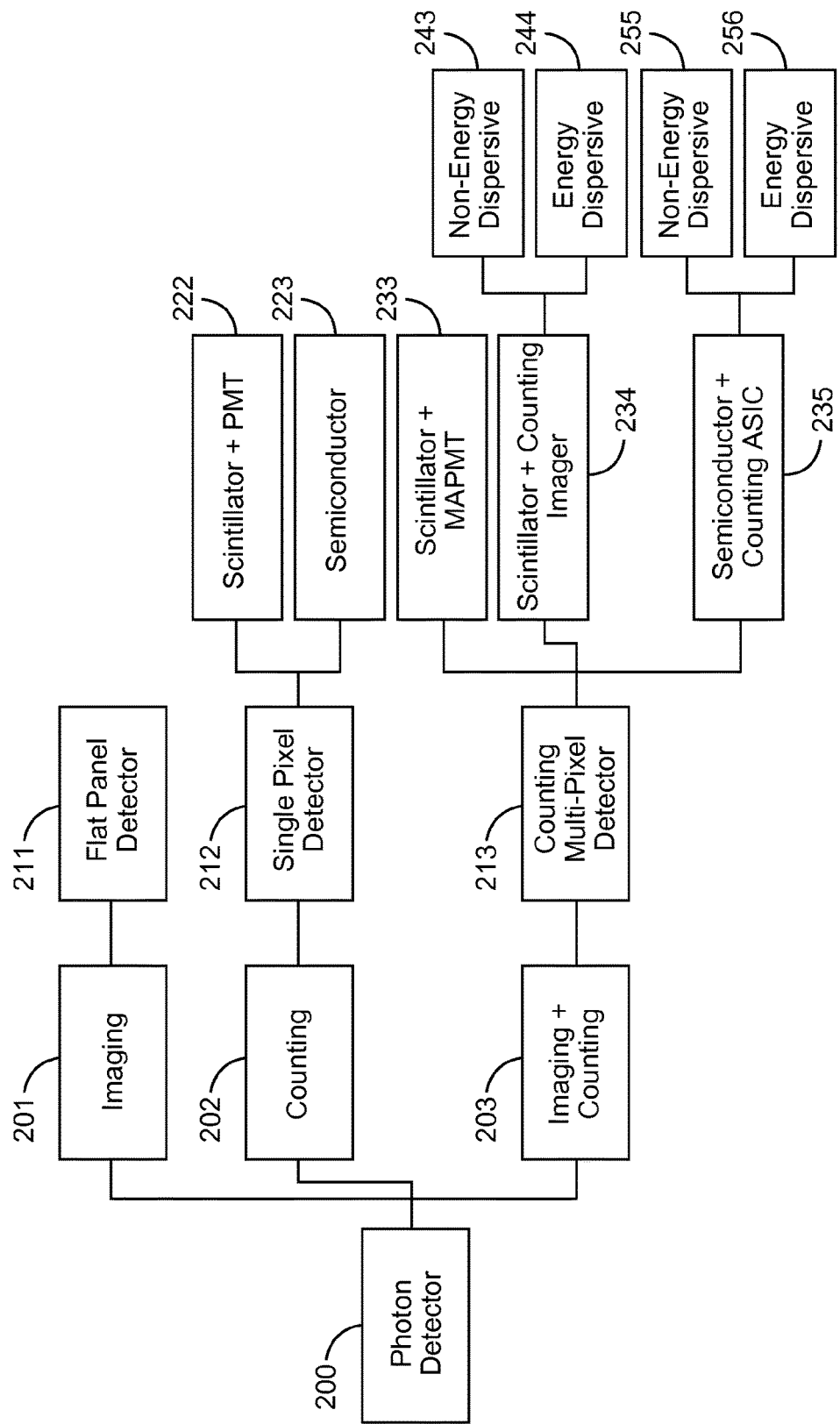
FIG. 2 is a diagram showing classifications of photon detectors in accordance with the device of FIG. 1.

The detector 103 may be a multi-element (i.e., multi-pixel) detector configured to perform photon counting. Each element of the detector 103 is shown having a width D. The multi-element capability records the energy spectrum at different depths within the materials 110-112 using a single measurement. The photon count capability of the detector 103 may record the photon count arriving at each element and the energy-dispersive capability sorts the count into different energy bins to generate a spectrum. Various detector embodiments are shown in FIG. 2 and discussed subsequently.

The photons entering the materials 110-112 are reflected back from certain points along a line 130 from the photon source 101. As the tool in which the device 100 is located rotates in the wellbore, this line 130 moves around the materials 110-112 encircling the wellbore so that the entire diameter of the borehole is investigated as the tool moves through the wellbore.

A housing (i.e., tool housing), accommodates both the detector 103 with collimator 105 and the source 101. The housing may be made of a shielding material (e.g., lead, tungsten) to prevent emitted photons from hitting the detector 103 directly and the collimator 105 is designed to allow detection of backscattered photons from the materials 110-112.

In an embodiment, the detector 103 may be a photon counting, multi-element photo-sensor that produces an electrical signal in response to scintillation lights or photons. However, various embodiments are not limited to any one type of detector. There are a plurality of different types of detectors that may be used, as illustrated in FIG. 2.

FIG. 2 is a diagram showing lists of classifications of photon detectors based on their functions. In general, there are three types of photon detectors 200: imaging 201, counting 202, and imaging with counting 203.

Photon imaging detectors 201 collect a total charge produced by the incident photons over a period of time. Photon imaging detectors 201 may generate a 2-D image of the object but may not detect the photon energy information. Examples of photon imaging detectors 201 include flat panel imaging detectors 211 used in medical and non-destructive testing industries.

Counting detectors 202 generate a count of the number of detected incident photons according to photon energies. This information may be used to generate an energy spectrum of the detected photons. The counting detector 202 may provide spectrum information for the detected photons, but may not have a sensitivity to the detected location on the detector. Examples of counting detectors 202 include single element detectors 212 such as a scintillator coupled with a photomultiplier tube 222 and a semiconductor photo diode 223.

Imaging and counting detectors 203 combine the advantages of the above two types of detectors 201, 202. The imaging and counting detectors 203 are counting multi-element detectors 213 that are configured to produce images of the detected photons with position information for each detected photon. In this case, each element can count every incident photon.

Due to complexity of fabrication, some sub-types of counting multi-element detectors 213 may only count photons above a particular energy threshold. These types of detectors are considered non-energy-dispersive detectors (i.e., cannot differentiate the energy of detected photons). Counting multi-element detectors 213 that can sort photons into different energy categories and generate a full spectrum are considered energy-dispersive detectors (i.e., can differentiate the energy of detected photons, thus resulting in a received spectrum of photon energies).

One detector couples a scintillator (continuous or pixelated) with a multi-anode photomultiplier tube (MAPMT) 233. The MAPMT is position-sensitive and records the photon counts and energy information through a multiple-channel (e.g., 4 channels, 8 channels) multi-channel analyzer (MCA).

Another detector couples a scintillator (continuous or pixelated) with a counting imager 234 (e.g., complementary metal oxide semiconductor (CMOS) imager, charged coupled device (CCD)). Such a counting imager 234 may be a non-energy dispersive counting imager 243 or an energy dispersive counting imager 244.

Yet another detector may be constructed by bump bonding a pixelated semiconductor chip to a solid state counting application specific integrated circuit (ASIC) readout, depicted as semiconductor chip 235. The semiconductor chip 235 may be Cd(Zn)Te or $HgI_2$ with pixelated Ohmic or Schottky contacts. The ASIC readout may be formed as arrays of pixels with multiple energy categories per channel, and may be fabricated with CMOS technology.

Such a semiconductor chip 235 may be a non-energy dispersive semiconductor chip 255 or an energy dispersive semiconductor chip 256. The energy-dispersive semiconductor chip 256 may achieve high image contrast through photon counting and materials information may be extracted through the spectrum information.

Figure 3:
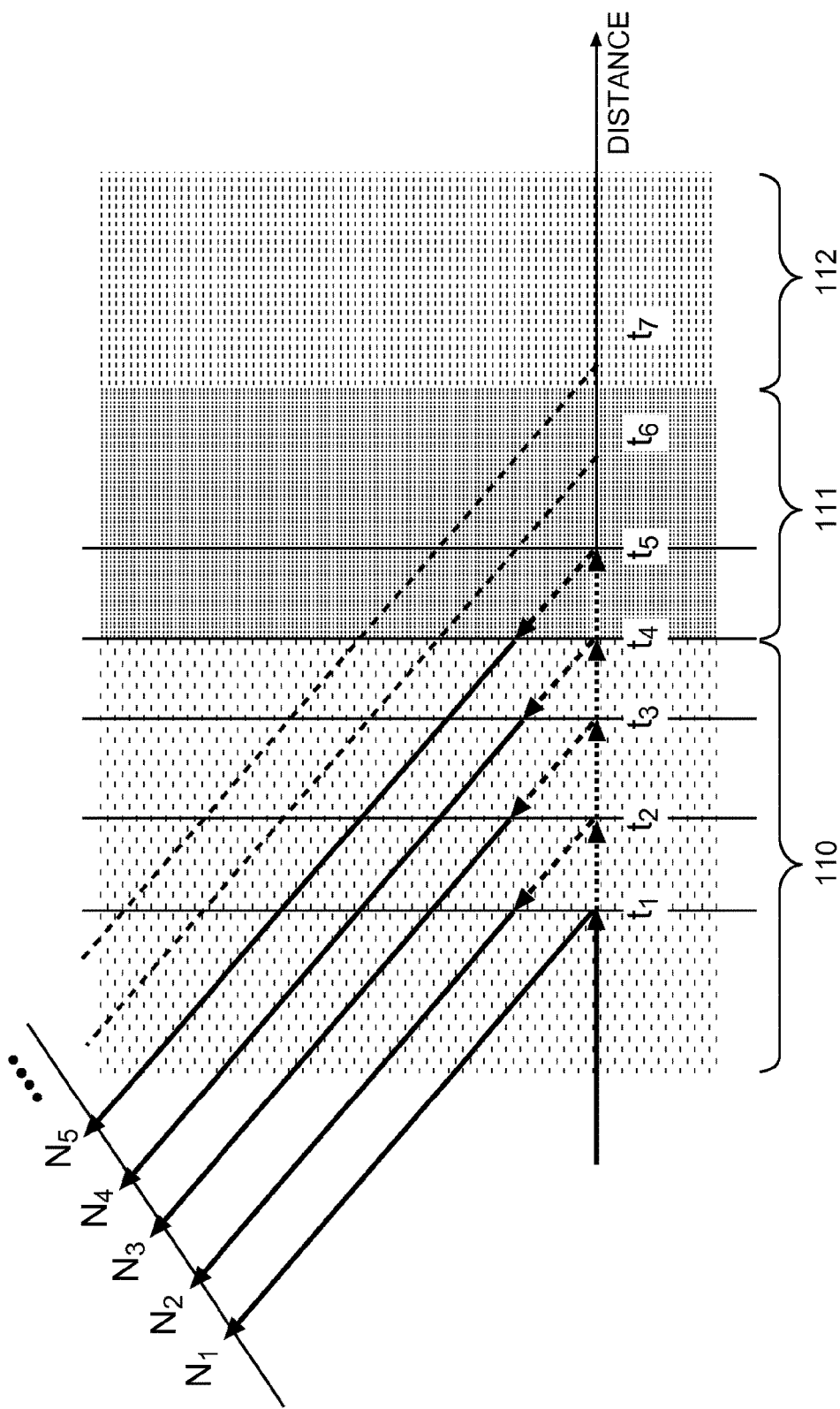
FIG. 3 is a diagram showing Compton backscattering events of emitted photons through multiple materials in accordance with the device of FIG. 1.

FIG. 3 is a diagram showing Compton backscattering events of emitted photons through multiple materials 110-112 in accordance with the device of FIG. 1. The backscattering events are shown with respect to distance $t_i$. In other words, photon $N_1$ is reflected back at distance $t_1$, photon $N_2$ is reflected back at distance $t_2$, photon $N_3$ is reflected back at distance $t_3$. This continues for distance $t_i$ through the materials 110-112 and for photon $N_i$. The materials 110-112 may be borehole fluid 110, casing 111 (e.g., steel), and cement 112. Other embodiments may have additional materials or different materials than those shown.

In the diagram of FIG. 3, $N_i$ represents the number of detected photons in the $i^{th}$ detector element after being Compton backscattered at the distance $t_i$ from the reference point (i.e., the face of the source and detectors as defined in FIG. 1). The detector elements have the same width, d, and, hence, each distance increases with the same increment, $$\frac{d}{\tan(\pi - \theta)}$$

as defined in FIG. 1. The differences between $N_i$ and $N_{i+1}$ can be explained by photon interactions along the extended travel path presented by dashed arrows. For example, $N_2$ is approximated to be proportional to a function expressed by:

$$N_2 \propto I_1 \times \qquad (1)$$
$$\left\{\rho_{m1} \times \exp\left(-\mu_{m1}(E) \times \frac{d}{\tan(\pi - \theta)}\right) \times \exp\left(-\mu_{m1}(E') \times \frac{d}{\sin(\pi - \theta)}\right)\right\} \times$$
$$\exp\left(-\mu_{m1}(E') \times \frac{t_1}{\cos(\pi - \theta)}\right)$$

Equation (1) assumes that the intensity of incoming photon of energy E is $I_1$ at $t_1$. $\rho_{m1}$ and $\mu_{m1}$ are density and linear attenuation coefficient of material 1, respectively. E' is calculated from the Compton equation when the initial photon energy and the scattering angle are known. All Compton backscattering events are occurring in the same material in this case and $N_3$ can be given by $$N_3 \propto I_2 \times \left\{\rho_{m1} \times \exp\left(-\mu_{m1}(E) \times \frac{d}{\tan(\pi - \theta)}\right) \times \right. \qquad (2)$$
$$\left. \exp\left(-\mu_{m1}(E') \times \frac{d}{\sin(\pi - \theta)}\right)\right\} \times \exp\left(-\mu_{m1}(E') \times \frac{t_2}{\cos(\pi - \theta)}\right) =$$
$$I_1 \times \exp\left(-\mu_{m1}(E) \times \frac{d}{\tan(\pi - \theta)}\right) \times$$
$$\left\{\rho_{m1} \times \exp\left(-\mu_{m1}(E) \times \frac{d}{\tan(\pi - \theta)}\right) \times \exp\left(-\mu_{m1}(E') \times \frac{d}{\sin(\pi - \theta)}\right)\right\} \times$$
$$\exp\left(-\mu_{m1}(E') \times \frac{t_1}{\cos(\pi - \theta)}\right) \times \exp\left(-\mu_{m1}(E') \times \frac{d}{\sin(\pi - \theta)}\right)$$

The ratio of $N_2$ to $N_3$ results in the equation:

$$\frac{N_2}{N_3} = \exp\left(-\mu_{m1}(E) \times \frac{d}{\tan(\pi - \theta)}\right) \times \exp\left(-\mu_{m1}(E') \times \frac{d}{\sin(\pi - \theta)}\right) \qquad (3)$$

$$\frac{N_i}{N_{i+1}} = \exp\left(-\mu_{m1}(E) \times \frac{d}{\tan(\pi - \theta)}\right) \times \exp\left(-\mu_{m1}(E') \times \frac{d}{\sin(\pi - \theta)}\right) = \qquad (4)$$
$$\text{Constant} = C_1$$

This ratio becomes a constant his ratio becomes a constant as long as both $N_i$ and $N_{i+1}$ result from Compton backscattering events within the same material and can be generalized to the equation: where $C_1$ is a constant determined by the property of a first material, such as borehole fluid 110. If there is a transition from one material (e.g., borehole fluid 110) to another (e.g., casing 111), (i.e., $N_4$ and $N_5$ as shown in FIG. 3), the equation for Ni can be $$\frac{N_i}{N_{i+1}}$$

arranged as follows:

$$\frac{N_i}{N_{i+1}} = \quad (5)$$
$$\frac{\rho_{m1}}{\rho_{m2}} \times \exp\left(-\mu_{m2}(E) \times \frac{d}{\tan(\pi-\theta)}\right) \times \exp\left(-\mu_{m2}(E') \times \frac{d}{\sin(\pi-\theta)}\right) =$$
$$\frac{\rho_{m1}}{\rho_{m2}} \times \text{Constant} = \frac{\rho_{m1}}{\rho_{m2}} \times C_2 = D_1$$

where $C_2$ is a constant determined by the property of casing 111. In the case of an x-ray tube source, the mean energy of the photon spectrum can be used and Equations (4) and (5) may be replaced by Equations (4') and (5'), respectively:

$$\frac{N_i}{N_{i+1}} = \exp\left(-\mu_{m1}(\bar{E}) \times \frac{d}{\tan(\pi-\theta)}\right) \times \exp\left(-\mu_{m1}(\bar{E}') \times \frac{d}{\sin(\pi-\theta)}\right) = C_1 \quad (4')$$

$$\frac{N_i}{N_{i+1}} = \frac{\rho_{m1}}{\rho_{m2}} \times \exp\left(-\mu_{m2}(\bar{E}) \times \frac{d}{\tan(\pi-\theta)}\right) \times \quad (5')$$
$$\exp\left(-\mu_{m2}(\bar{E}') \times \frac{d}{\sin(\pi-\theta)}\right) = \frac{\rho_{m1}}{\rho_{m2}} \times C_2 = D_1$$

Figure 4:
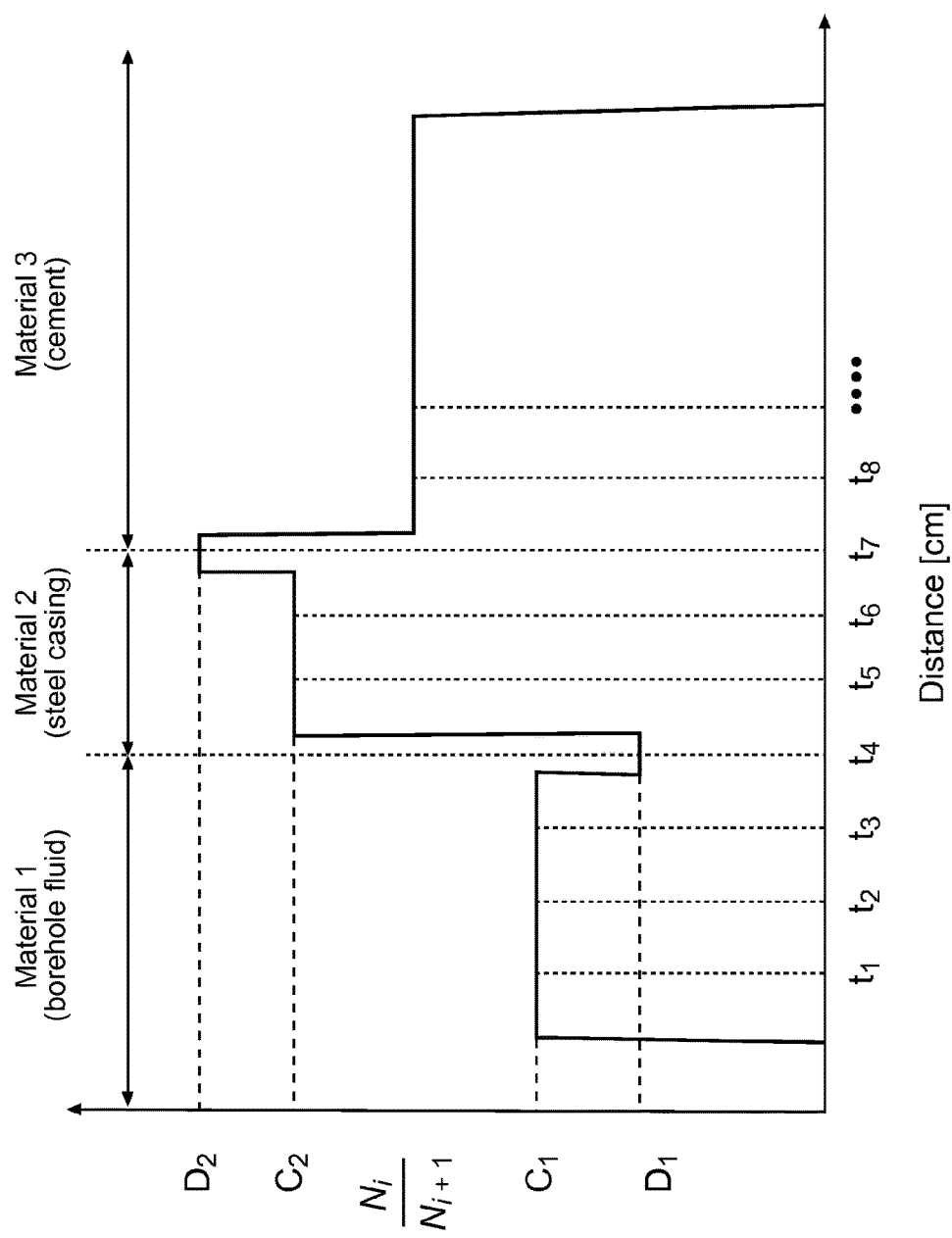
FIG. 4 is a plot showing a theoretical distribution of ratio values in various materials in accordance with the device of FIG. 1.

A distribution of ratio values for the geometry shown in FIG. 3 may be constructed as shown in FIG. 4 under ideal conditions. FIG. 4 is a plot showing a theoretical distribution of ratio values in accordance with the device of FIG. 1. The distance through the materials is shown along the x-axis while the $$\frac{N_i}{N_{i+1}}$$

ratio is shown along the y-axis.

For purposes of the distribution, the three materials 110-112 are assumed to be borehole fluid, casing (e.g., steel), and cement, respectively. For a given detector geometry, distance to a material boundary is given by $$\frac{H}{\tan(\pi-\theta)},$$

where H is the height of the detector element, above the centerline of the photon beam, whose ratio value is corresponding to either a valley ($D_1$) or a peak ($D_2$). The uncertainty of the determined distance is $$\pm\frac{d/2}{\tan(\pi-\theta)}.$$

The accuracy of the computation is on the order of millimeters, or sub-millimeters when using a high resolution semiconductor photon detector having a pixel size on the order of a millimeter or less. Similarly, this accuracy assumes a collimator having comparable dimensions to the detector. In addition, the density of borehole fluid 110 can be deduced from $$\frac{D_1}{C_2}$$

in the cased-hole since the density of steel casing 111, $\rho_{m2}$, is known.

Figure 5:
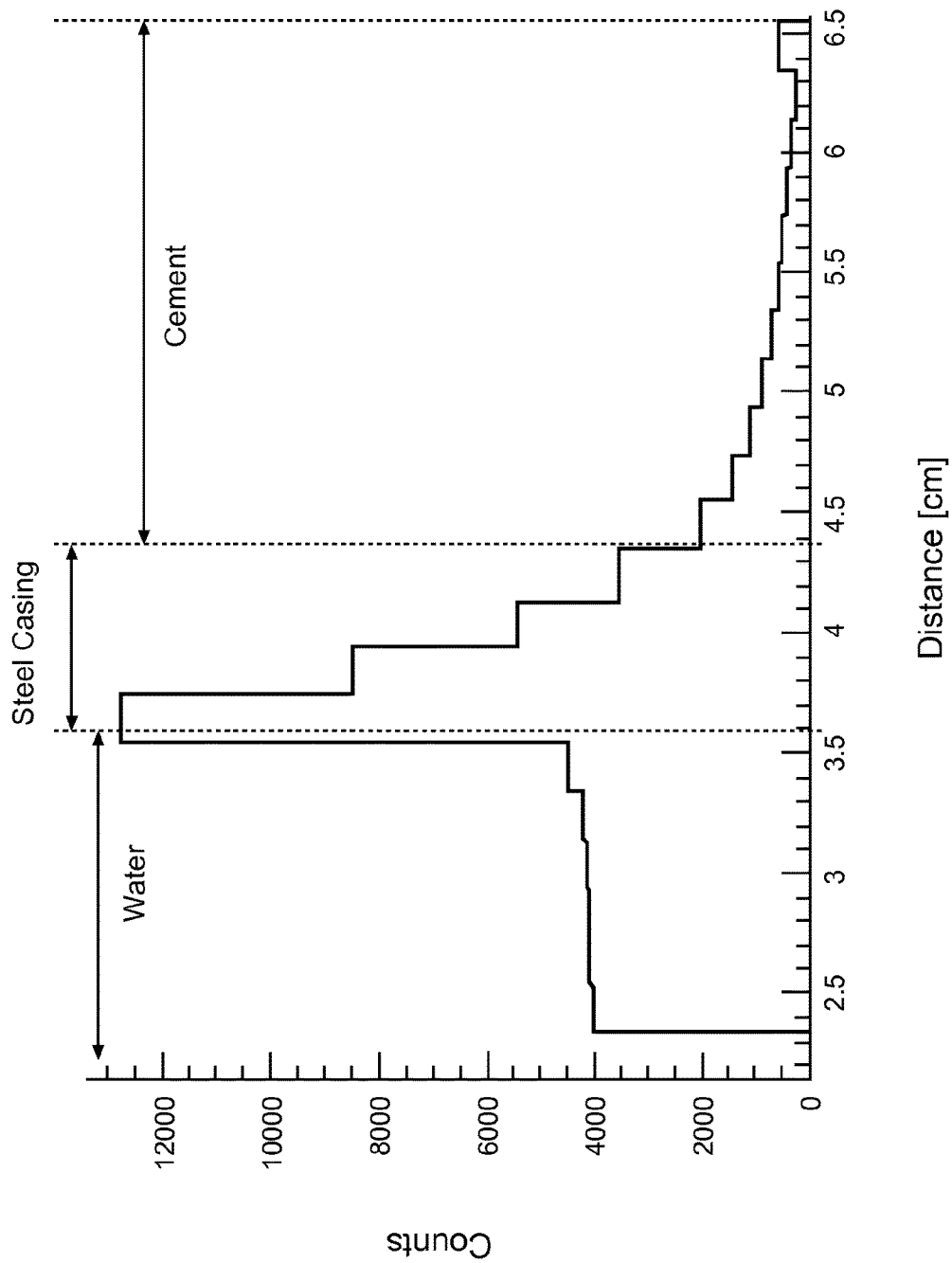
FIG. 5 is a plot showing a distribution of measured photon counts in the detector in accordance with the device of FIG. 1.

FIG. 5 is a plot showing a distribution of measured photon counts in the detector array in accordance with the device of FIG. 1. This plot shows the distance, in centimeters, along the x-axis and the photon counts along the y-axis. This figure shows the results from a Monte Carlo simulation in accordance with the device of FIG. 1, assuming water as the borehole material. The size of each detector element was assumed to be 2 mm in width and the collimator angle was set to detect Compton backscattering at 135 degrees. This figure shows the distribution of measured Compton backscattered photons through the materials.

Figure 6:
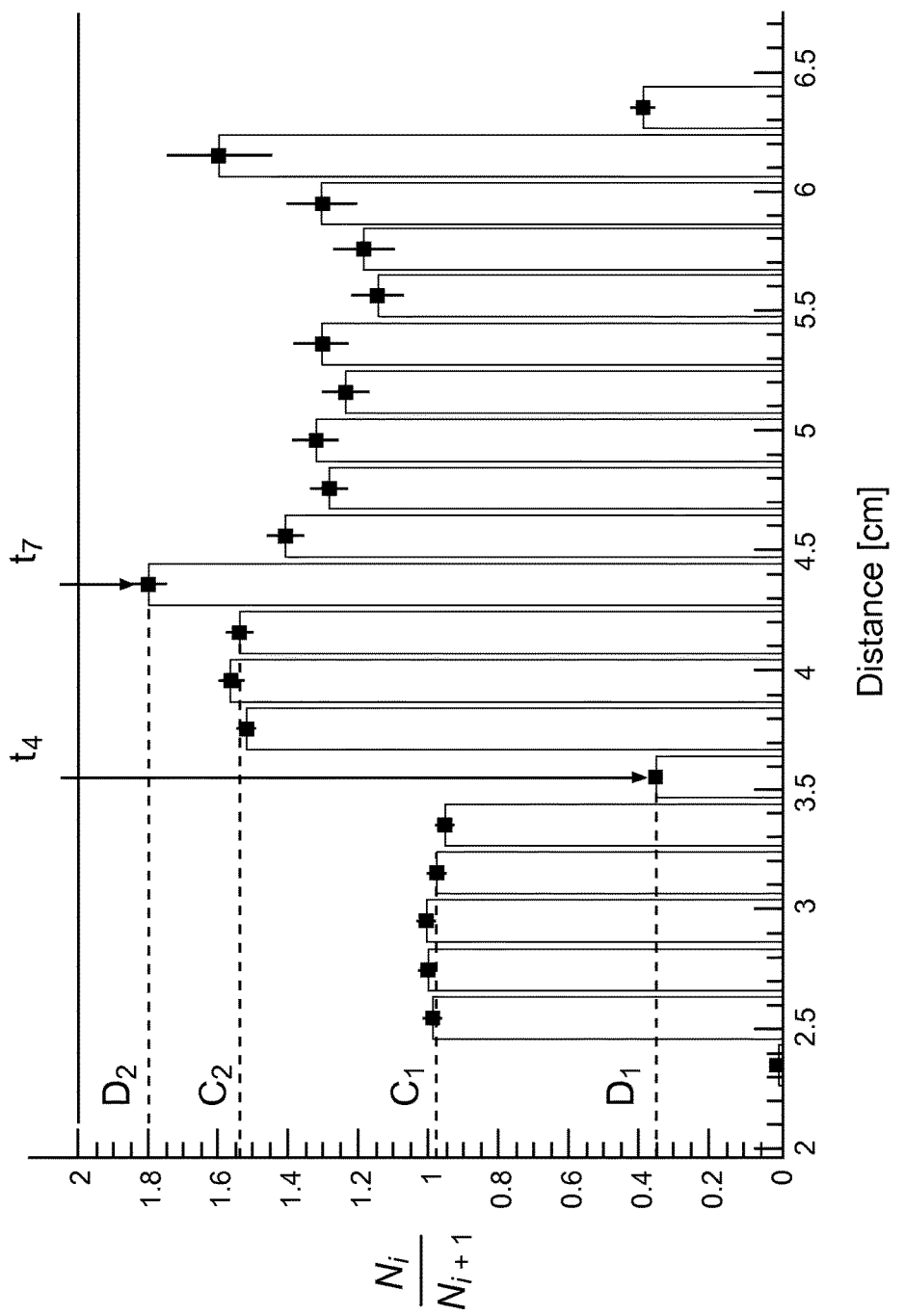
FIG. 6 is a plot showing a constructed distribution of ratio values based on Monte Carlo simulations in accordance with the device of FIG. 1.

FIG. 6 is a plot showing a constructed distribution of ratio values based on Monte Carlo simulations in accordance with the device of FIG. 1. This plot shows the distance, in centimeters, along the x-axis and the $$\frac{N_i}{N_{i+1}}$$

ratio along the y-axis.

FIG. 6 shows the ratio of counts in $i^{th}$ bin to $(i+1)^{th}$ bin. The simulation plot of FIG. 6 may be compared to the theoretical plot of FIG. 4 to illustrate that the simulation is substantially in agreement with the theoretical prediction. However, the simulation results may deviate from the theoretical results as the distance increases. Values for $C_1$, $C_2$, $D_1$ and $D_2$ are seen in this figure.

$$\frac{D_1}{C_2}$$

value is expected to be proportional to the density of borehole material as shown in Equation (5). This relationship remains valid as long as there is a contrast in densities between the borehole material and the casing. One application of this feature could be determination of the borehole fluid density, since most common borehole materials include drilling muds. In addition, large contrasts in density between borehole fluids and casings are suitable for in situ borehole fluid density measurements. This eliminates the need for prior knowledge of borehole fluid density in use.

The Monte Carlo simulation results of different borehole fluids result in plots of different shapes. For example, sodium (Na) formate brine has a density of 1.330 grams/cubic centimeter ($g/cm^3$) resulting in a $C_2$ of 1.494, a $D_1$ of 0.427 and a ratio $$\frac{D_1}{C_2} \text{ of } 0.286.$$

As another example, cesium (Cs) formate brine has a density of 2.301 g/cm³ resulting in a $C_2$ of 1.292, a $D_1$ of 0.681, and a ratio $$\frac{D_1}{C_2} \text{ of } 0.527.$$

Other materials may result in different values. $D_1$ and $C_2$ values were obtained from the distributions of ratio values and the ratio values of $$\frac{D_1}{C_2}$$

were correlated to the material densities. As a result, a measurement in a cased hole will reveal the material density based on this correlation function. The boundary between the borehole material and the steel casing, $t_4$, was determined to be 3.55±0.1 cm while its true value is 3.6 cm. Also the boundary between the steel casing and the cement, $t_7$, was found to be 4.35±0.1 cm while its true value is 4.362 cm.

Figure 7:
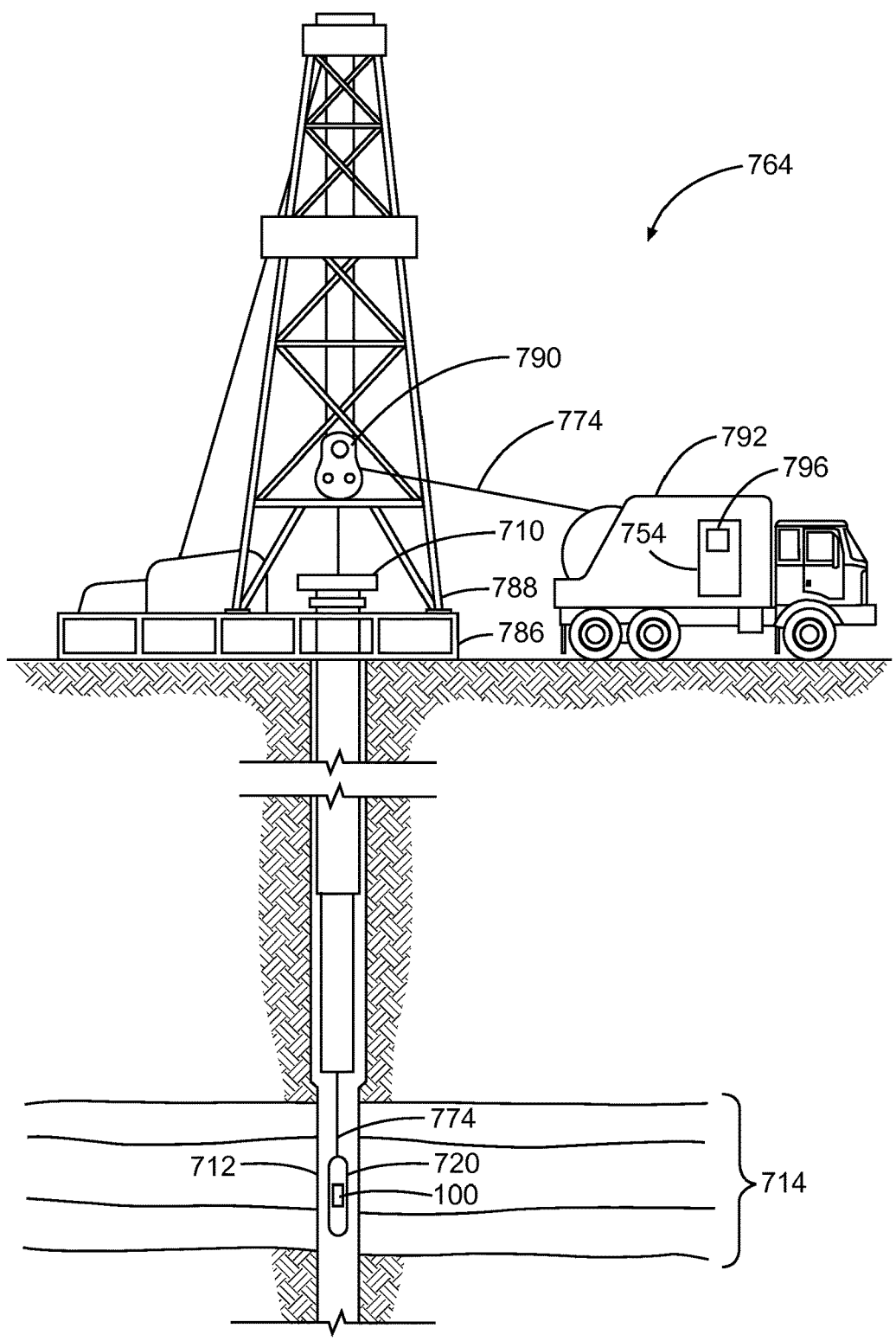
FIG. 7 is a diagram showing a wireline system, according to various embodiments.
Figure 8:
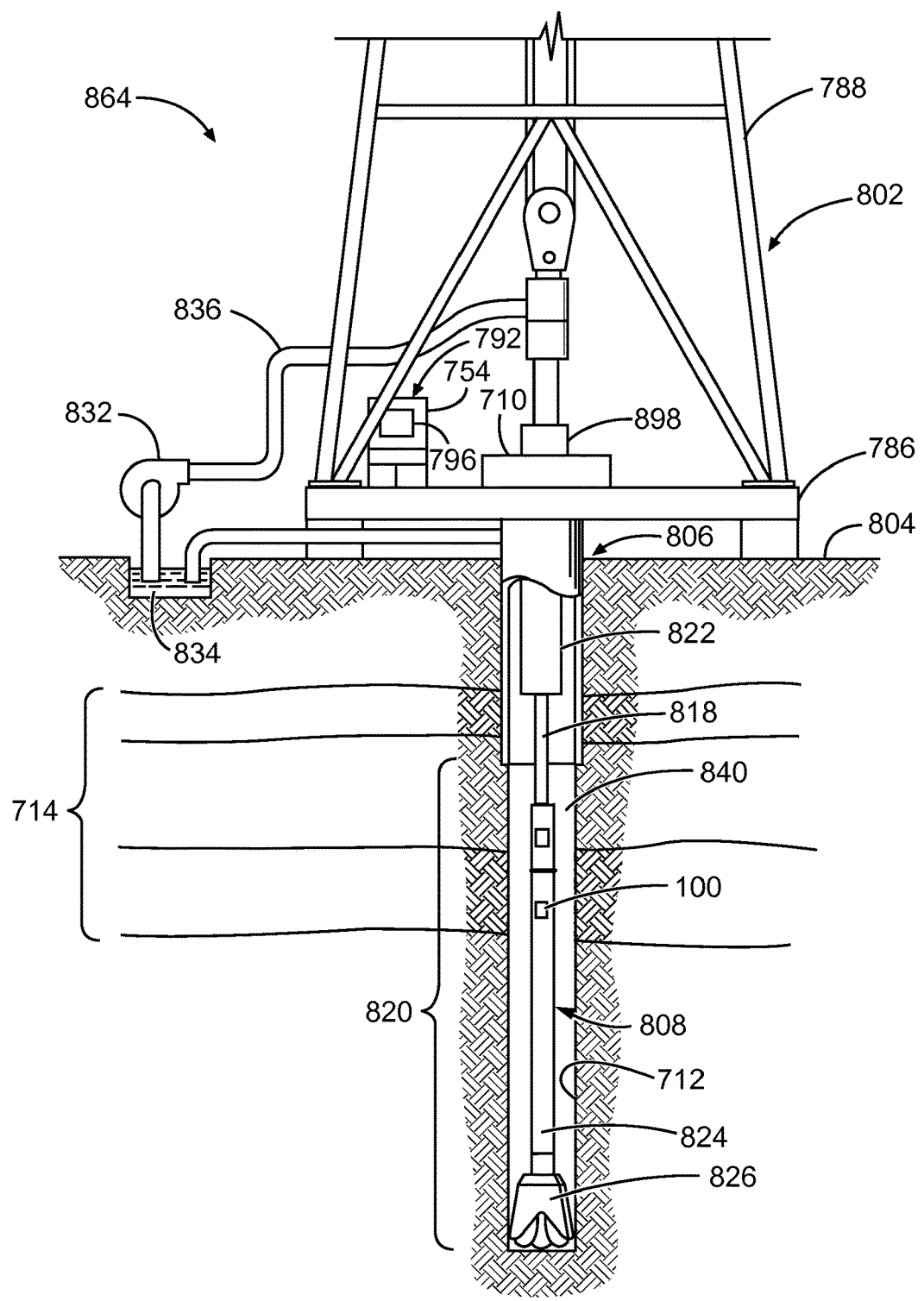
FIG. 8 is a diagram showing a drilling system, according to various embodiments.

FIG. 7 is a diagram showing a wireline system 764 and FIG. 8 is a diagram showing a drilling system 864. The systems 764, 864 may thus comprise portions of a wireline logging tool housing 720 as part of a wireline logging operation or of a downhole tool housing 824 as part of a drilling operation. Either of these tool housings 720, 824 may include the device 100 to determine tool standoff and material density in a borehole as described previously.

FIG. 7 illustrates a drilling platform 786 equipped with a derrick 788 that supports a hoist 790. Drilling oil and gas wells is commonly carried out using a string of drill pipes connected together so as to form a drillstring that is lowered through a rotary table 710 into a wellbore or borehole 712. Here it is assumed that the drillstring has been temporarily removed from the borehole 712 to allow a wireline logging tool housing 720, such as a probe or sonde with the device 100 to determine tool standoff and material density in a borehole, to be lowered by wireline or logging cable 774 (e.g., slickline cable) into the borehole 712. Typically, the wireline logging tool housing 720 is lowered to the bottom of the region of interest and subsequently pulled upward at a substantially constant speed.

During the upward trip, at a series of depths, various instruments may be used to perform measurements on the borehole material, casing and cement lining the borehole 712. The wireline data may be communicated to a surface logging facility 792 for processing, analysis, and/or storage. The logging facility 792 may be provided with electronic equipment for various types of signal processing. Similar formation evaluation data may be gathered and analyzed during drilling operations (e.g., during LWD/MWD operations, and by extension, sampling while drilling).

In some embodiments, the tool housing 720 is suspended in the wellbore by a wireline cable 774 that connects the tool to a surface control unit (e.g., comprising a workstation 754). The tool may be deployed in the borehole 712 on coiled tubing, jointed drill pipe, hard wired drill pipe, or any other suitable deployment technique.

Referring to FIG. 8, it can be seen how a system 864 may also form a portion of a drilling rig 802 located at the surface 804 of a well 806. The drilling rig 802 may provide support for a drillstring 808. The drillstring 808 may operate to penetrate the rotary table 710 for drilling the borehole 712 through the subsurface formations 714. The drillstring 808 may include a drill pipe 818 and a bottom hole assembly 820 (e.g., drill string), perhaps located at the lower portion of the drill pipe 818.

The bottom hole assembly 820 may include drill collars 822, a downhole tool housing 824 including the device 100 to determine tool standoff and borehole material density in a borehole, and a drill bit 826. The drill bit 826 may operate to create the borehole 712 by penetrating the surface 804 and the subsurface formations 714. The downhole tool housing 824 may comprise any of a number of different types of tools besides the device 100 including MWD tools, LWD tools, and others.

During drilling operations, the drillstring 808 (perhaps including the drill pipe 818 and the bottom hole assembly 820) may be rotated by the rotary table 710. Although not shown, in addition to, or alternatively, the bottom hole assembly 820 may also be rotated by a motor (e.g., a mud motor) that is located down hole. The drill collars 822 may be used to add weight to the drill bit 826. The drill collars 822 may also operate to stiffen the bottom hole assembly 820, allowing the bottom hole assembly 820 to transfer the added weight to the drill bit 826, and in turn, to assist the drill bit 826 in penetrating the surface 804 and subsurface formations 714.

During drilling operations, a mud pump 832 may pump drilling fluid (sometimes referred to as "drilling mud") from a mud pit 834 through a hose 836 into the drill pipe 818 and down to the drill bit 826. The drilling fluid can flow out from the drill bit 826 and be returned to the surface 804 through an annular area 840 between the drill pipe 818 and the sides of the borehole 712. The drilling fluid may then be returned to the mud pit 834, where such fluid is filtered. In some embodiments, the drilling fluid can be used to cool the drill bit 826, as well as to provide lubrication for the drill bit 826 during drilling operations. Additionally, the drilling fluid may be used to remove subsurface formation cuttings created by operating the drill bit 826.

The workstation 754 and the controller 796 may include modules comprising hardware circuitry, a processor, and/or memory circuits that may store software program modules and objects, and/or firmware, and combinations thereof. The workstation 754 and controller 796 may be configured to create a density and energy spectrum map of the borehole cement.

In various embodiments, components of a system operable to conduct standoff distance and borehole material density measurements and analyze the measurements as described herein or in a similar manner, can be realized in combinations of hardware and/or processor executed software. These implementations can include a machine-readable storage device having machine-executable instructions, such as a computer-readable storage device having computer-executable instructions. Further, a computer-readable storage device may be a physical device that stores data represented by a physical structure within the device. Such a physical device is a non-transitory device. Examples of machine-readable storage devices can include, but are not limited to, read only memory (ROM), random access memory (RAM), a magnetic disk storage device, an optical storage device, a flash memory, and other electronic, magnetic, and/or optical memory devices.

Figure 9:
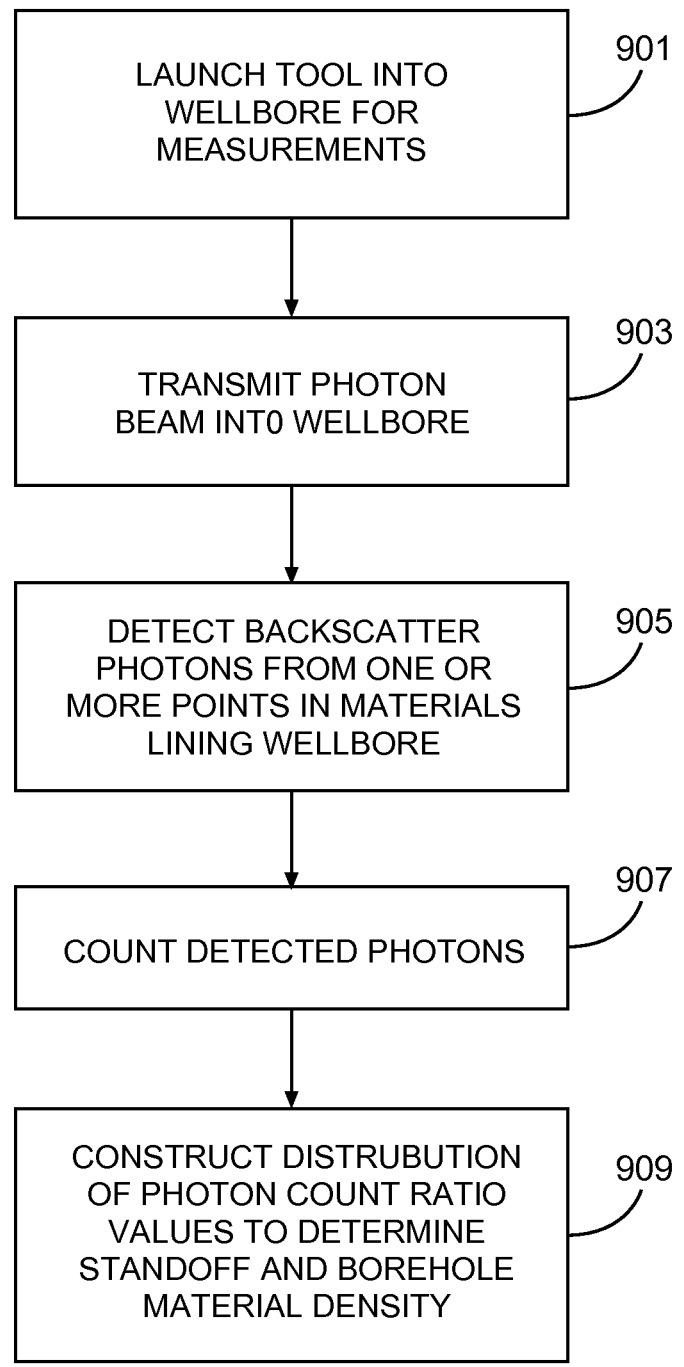
FIG. 9 is a flowchart showing an embodiment of a method for determining tool standoff and material density in a borehole.

FIG. 9 is a flowchart showing an embodiment of a method for determining tool standoff and borehole material density in a borehole. In 901, a tool comprising the device to determine tool standoff and borehole material density in a borehole is lowered into the wellbore to be inspected. The tool may be part of a wireline tool or a drill string tool, as described subsequently.

In 903, a photon beam is transmitted into the wellbore in the direction of the casing and cement. This may be performed while the tool is spinning so that a three dimensional mapping of the cement density may be performed.

In 905, a photon detector (e.g., an energy dispersive multi-element area detector) is used with a collimator to detect backscatter photons from one or more reflection points in the wellbore materials. As discussed previously, only those photons that are reflected back at the angle determined by the collimator are detected, thus providing the detector with a photon count of particular reflection points in the materials. The power of the photon beam may be adjusted as necessary to penetrate the various materials. For example, if the number of detected photons has not reached a particular threshold, the photon beam power may be increased.

In 907, the backscatter photons received from the reflection point in the cement, only at the angle of the collimator, are counted. The quantity of photons provides an indication of material density, as seen previously with respect to the plot of FIG. 4.

In 909, a distribution of photon count ratio values is constructed. The distribution (e.g., FIG. 4) may provide indications of the densities of various materials. The change in densities provides an indication as to the boundaries between the different materials. For example, referring to FIG. 4, it can be seen that the change in density from material 1 (borehole fluid) to material 2 (steel casing) is indicated by the value of the ratio $$\frac{D_1}{C_2}$$

at time $t_4$. Thus, $t_4$ is the tool standoff distance.

Tool standoff is typically measured by acoustic tools where the acoustic penetrating power is challenged by heavy mud and thick steel casing. As a matter of contrast, the above-disclosed method employs a nuclear method of Compton scattering of photons to overcome limitations of the traditional standoff measurement tools in heavy fluid. This method may identify boundaries of surrounding materials in the downhole environment by adjusting the energy of a photon source to see through heavy mud and even thick steel casing to identify the steel casing/cement boundary. Effects of heavy mud and thick steel casing could be mitigated in this method by selection of a higher energy photon source with higher penetrating power. Using high resolution semiconductor detector technologies, the precision and accuracy of the determined standoff may be on the order of millimeters or less. When the steel casing is in place, this method is able to determine standoff and borehole material density simultaneously, and can provide useful information (e.g., borehole material density and standoff) to environmental correction algorithms.

Figure 10:
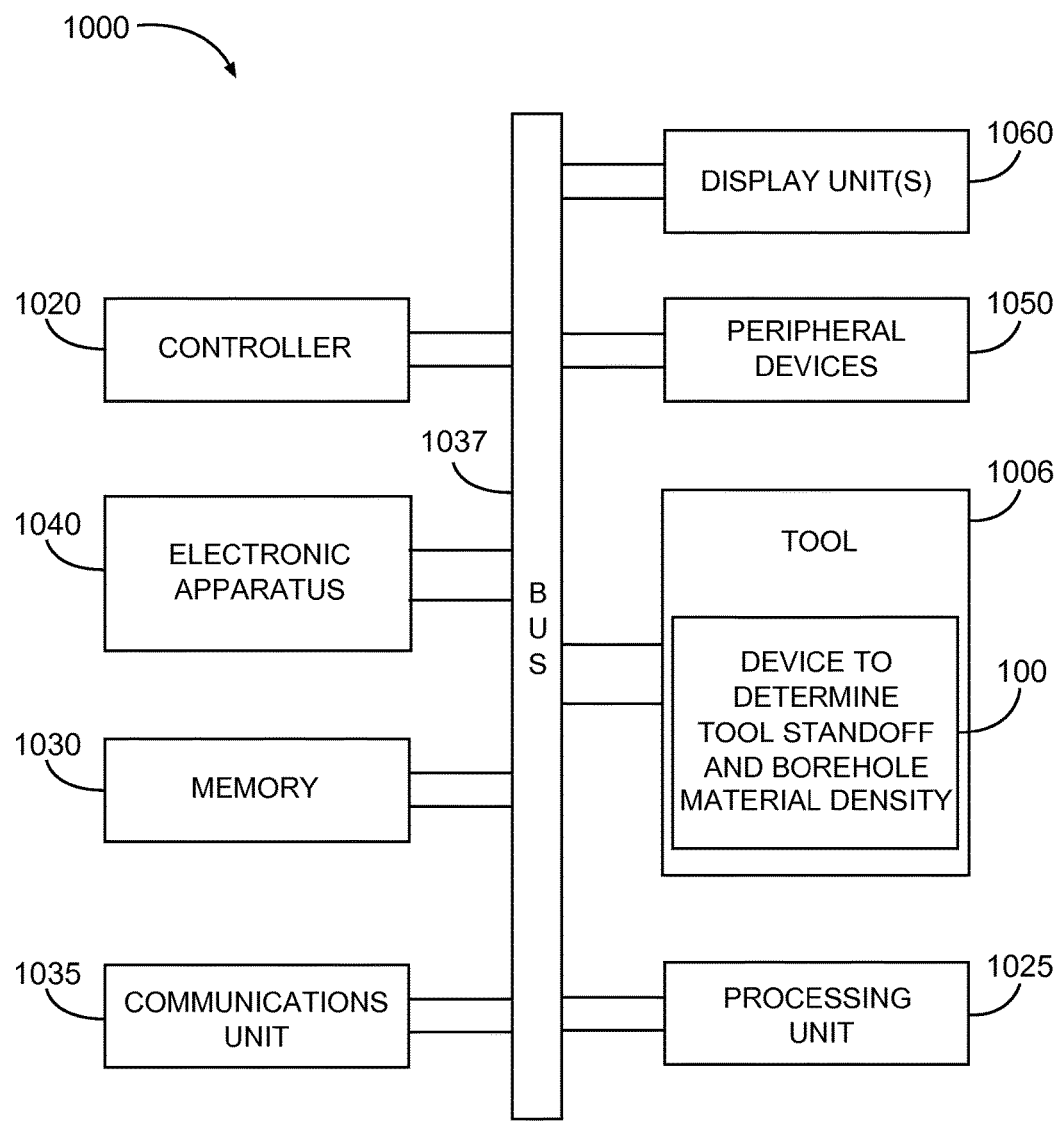
FIG. 10 is a block diagram of an example system operable to execute the method of FIG. 9.

FIG. 10 is a block diagram of an example system 1000 operable to execute the method of FIG. 9. The system 1000 may include a tool housing 1006 with a device 100 having a photon source 101 and detector 103 with slanted collimator 105 such as illustrated in FIG. 1. The system 1000 may be configured to operate in accordance with the teachings herein to determine tool standoff and borehole material density in a downhole environment.

The system 1000 may include a controller 1020, a memory 1030, an electronic apparatus 1040, and a communications unit 1035. The memory 1030 can be structured to include a database. The controller 1020, the memory 1030, and the communications unit 1035 can be arranged to operate as a processing unit to control operation of the tool 1006 and execute steps to perform the method of FIG. 9. A processing unit 1025, structured to conduct such evaluation using neutron-neutron measurements, can be implemented as a single unit or distributed among the components of the system 1000 including electronic apparatus 1040. The electronic apparatus 1040 can provide other circuitry for operation of the system 1000. The controller 1020 and the memory 1030 can operate to control activation of the neutron source(s) in the device 100 to generate neutron pulses. The controller 1020 and the memory 1030 can operate to control selection of the detector(s) in the device 100 and to manage processing schemes. The controller 1020, the memory 1030, and other components of the system 1000 can be configured, for example, to operate similar to or identical to the components discussed herein or similar to or identical to any of methods discussed herein.

The communications unit 1035 can include downhole communications for appropriately located sensors in a wellbore. Such downhole communications can include a telemetry system. The communications unit 1035 may use combinations of wired communication technologies and wireless technologies at frequencies that do not interfere with on-going measurements.

The system 1000 can also include a bus 1037, where the bus 1037 provides electrical conductivity among the components of the system 1000. The bus 1037 can include an address bus, a data bus, and a control bus, each independently configured or in an integrated format. The bus 1037 can be realized using a number of different communication mediums that allows for the distribution of components of the system 1000. The bus 1037 can include a network. Use of the bus 1037 can be regulated by the controller 1020.

In various embodiments, the peripheral devices 1050 can include additional storage memory and other control devices that may operate in conjunction with the controller 1020 and the memory 1030. In an embodiment, the controller 1020 can be realized as a processor or a group of processors that may operate independently depending on an assigned function.

The system 1000 can include display unit(s) 1060 as a distributed component on the surface of a wellbore, which can be used with instructions stored in the memory 1030 to implement a user interface to monitor the operation of the tool 1006 or components distributed within the system 1000. The user interface may be used to input parameter values for thresholds such that the system 1000 can operate autonomously, without user intervention in a variety of applications. The user interface can also provide for manual override and change of control of the system 1000 to a user. Such a user interface can be operated in conjunction with the communications unit 1035 and the bus 1037. Many embodiments may thus be realized, and the elements of several will now be listed in detail.

Example 1 is a downhole tool comprising: a photon beam source configured to transmit a photon beam into a wellbore; a photon detector configured to count detected photons received at a predetermined angle from materials lining the wellbore; and a controller, coupled to the photon beam source and the photon detector, configured to determine a density of a borehole material based on a number of detected photons received at the predetermined angle.

In Example 2, the subject matter of Example 1 may further include a downhole tool wherein the detector is a multi-element photon detector.

In Example 3, the subject matter of Examples 1-2 may further include a detector collimator coupled to the detector and configured such that only photons received at the predetermined angle are detected by the detector.

In Example 4, the subject matter of Examples 1-3 may further include a downhole tool wherein the photon beam source comprises an X-ray tube, a chemical source, or a gamma-ray source.

In Example 5, the subject matter of Examples 1-4 may further include a downhole tool wherein the detector is a photo-sensor configured to generate an electrical signal in response to scintillation photons.

In Example 6, the subject matter of Examples 1-5 may further include a tool housing to contain the photon beam source and photon detector wherein the tool housing comprises a photon shielding material.

In Example 7, the subject matter of Examples 1-6 may further include a controller configured to determine a plurality of photon count ratio values, construct a distribution of the photon ratio values with respect to distance from the tool, and determine a standoff distance between the tool and a wellbore casing based on a photon count ratio value indicating a change from a first material to a second material.

In Example 8, the subject matter of Examples 1-7 may further include a downhole tool wherein the first material is the borehole material indicated by a first photon count ratio and the second material is the wellbore casing indicated by a second photon count ratio, wherein the first photon count ratio is less than the second photon count ratio.

Example 9 is a method for determining tool standoff distance and material density in a wellbore, the method comprising: transmitting a photon beam at a first predetermined angle to the wellbore; detecting, using a multi-element photon detector, backscatter photons received at a second predetermined angle from materials lining the wellbore; counting a number of photons detected at the second predetermined angle to generate a distribution of photon count ratio values; and determining the standoff distance and borehole material density in response to a change in photon count ratio values of the distribution of photon count ratio values.

In Example 10, the subject matter of Example 9 may further include a method wherein a first photon count ratio value $D_1$ indicates a valley in the distribution and a second photon count ratio value $C_2$ indicates a density of wellbore casing such that the standoff distance is indicated by $$\frac{D_1}{C_2}.$$

In Example 11, the subject matter of Examples 9-10 may further include determining the borehole material density in response to $$\frac{D_1}{C_2}.$$

In Example 12, the subject matter of Examples 9-11 may further include a method wherein the distribution of photon count ratio values comprises $$\frac{N_i}{N_{i+1}}$$

wherein $N_i$ represents a number of detected photons at an $i^{th}$ element of the photon detector and $N_{i+1}$ represents a number of detected photons at an $i^{th}+1$ element of the photon detector.

In Example 13, the subject matter of Examples 9-12 may further include a method wherein the number of detected photons detected at the $i^{th}$ and $i^{th}+1$ elements are backscattered at distances $t_i$ and $t_{i+1}$, respectively, from a source of the photon beam and wherein the distances are different.

In Example 14, the subject matter of Examples 9-13 may further include determining a distance from the detector to a boundary between materials in response to $$\frac{H}{\tan(\pi - \theta)}$$

wherein $\theta$ represents the second predetermined angle and $H$ represents a height of a detector element, above a centerline of the photon beam, whose photon count ratio value corresponds to either a valley or a peak of the distribution of photon count ratio values.

In Example 15, the subject matter of Examples 9-14 may further include a method wherein the first predetermined angle is substantially 90°.

In Example 16, the subject matter of Examples 9-15 may further include transmitting the photon beam in a downhole environment from a wireline tool or a drill string tool.

In Example 17, the subject matter of Examples 9-16 may further include rotating the wireline tool or the drill string tool rotate such that the photon beam is rotated within the wellbore.

Example 18 is a system comprising a downhole tool including a device to determine tool standoff distance and material density in a borehole, the device comprising: a photon beam source configured to transmit a photon beam; a multi-element photon detector configured to count detected backscattered photons received at a predetermined angle from materials lining the wellbore; and a controller, coupled to the detector and the photon beam source, configured to control the photon beam source and detector and to determine the material density in the wellbore and the tool standoff distance from wellbore casing based on a plurality of photon count ratio values.

In Example 19, the subject matter of Example 18 may further include a system wherein the downhole tool is a wireline tool.

In Example 20, the subject matter of Examples 18-19 may further include a system wherein the downhole tool is a drillstring tool.

Although specific embodiments have been illustrated and described herein, it will be appreciated by those of ordinary skill in the art that any arrangement that is calculated to achieve the same purpose may be substituted for the specific embodiments shown. Various embodiments use permutations and/or combinations of embodiments described herein. It is to be understood that the above description is intended to be illustrative, and not restrictive, and that the phraseology or terminology employed herein is for the purpose of description. Combinations of the above embodiments and other embodiments will be apparent to those of skill in the art upon studying the above description.

What is claimed is:

1. A downhole tool comprising:
a photon beam source configured to transmit a photon beam into a wellbore;
a photon detector configured to count detected photons received at a predetermined angle from one or more backscattering events occurring at materials lining the wellbore; and
a controller, coupled to the photon beam source and the photon detector, configured to determine a density of a material based, at least in part, on a number of detected photons received at the predetermined angle and a distance between the photon detector and the backscattering events, wherein the distance is determined utilizing the predetermined angle, wherein the controller is further configured to determine a plurality of photon count ratio values, construct a distribution of the photon ratio values with respect to distance from the tool, and determine a standoff distance between the tool and a wellbore casing based on a photon count ratio value indicating a change from a first material to a second material.

2. The downhole tool of claim 1, wherein the detector is a multi-element photon detector.

3. The downhole tool of claim 1, further comprising a detector collimator coupled to the detector and configured such that only photons received at the predetermined angle are detected by the detector.

4. The downhole tool of claim 1, wherein the photon beam source comprises an X-ray tube, a chemical source, or a gamma-ray source.

5. The downhole tool of claim 1, wherein the detector is a photo-sensor configured to generate an electrical signal in response to scintillation photons.

6. The downhole tool of claim 1, further comprising a tool housing to contain the photon beam source and photon detector wherein the tool housing comprises a photon shielding material.

7. The downhole tool of claim 1, wherein the first material is a material indicated by a first photon count ratio and the second material is the wellbore casing indicated by a second photon count ratio, wherein the first photon count ratio is less than the second photon count ratio.

8. A method for determining tool standoff distance and material density in a wellbore, the method comprising:
transmitting a photon beam at a first predetermined angle to the wellbore;
detecting, using a multi-element photon detector, backscatter photons received at a second predetermined angle from materials lining the wellbore;
counting a number of photons detected by each element of the multi-element photon detector at the second predetermined angle to generate a distribution of photon count ratio values; and
determining the standoff distance and material density based, at least in part, on a change in photon count ratio values of the distribution of photon count ratio values and a distance between the photon detector and the backscattering events, wherein the distance is determined utilizing the predetermined angle.

9. The method of claim 8, wherein a first photon count ratio value $D_1$ indicates a valley in the distribution and a second photon count ratio value $C_2$ indicates a density of wellbore casing such that the standoff distance is indicated by a ratio $$\frac{D_1}{C_2}.$$

10. The method of claim 9, further comprising determining the material density based on the ratio $$\frac{D_1}{C_2}.$$

11. The method of claim 8, wherein the distribution of photon count ratio values comprises a ratio $$\frac{N_i}{N_{i+1}},$$

and wherein $N_i$ represents a number of detected photons at an $i^{th}$ element of the photon detector and $N_{i+1}$ represents a number of detected photons at an $i^{th}+1$ element of the photon detector.

12. The method of claim 11, wherein the number of detected photons detected at the $i^{th}$ and $i^{th}+1$ elements are backscattered at distances $t_i$ and $t_{i+1}$, respectively, from a source of the photon beam and wherein the distances are different.

13. The method of claim 11, further comprising transmitting the photon beam from a wireline tool or a drill string tool.

14. The method of claim 13, further comprising rotating the wireline tool or the drill string tool to rotate the photon beam within the wellbore.

15. The method of claim 8, further comprising determining a distance from the detector to a boundary between materials in response to $$\frac{H}{\tan(\pi - \theta)}$$

wherein θ represents the second predetermined angle and H represents a height of a detector element, above a centerline of the photon beam, whose photon count ratio value corresponds to either a valley or a peak of the distribution of photon count ratio values.

16. The method of claim 15, wherein the first predetermined angle is substantially 90 degrees.

17. A system comprising:
a downhole tool including a device to determine tool standoff distance and material density in a wellbore, the device comprising:
a photon beam source configured to transmit a photon beam;
a multi-element photon detector configured to count, for each element in the multi-element photon detector, detected backscattered photons received at a predetermined angle from materials lining the wellbore; and
a controller, coupled to the detector and the photon beam source, configured to control the photon beam source and detector and to determine a material density in the wellbore and the tool standoff distance from wellbore casing based, at least in part, on a plurality of photon count ratio values and a distance between the photon detector and the backscattering events, wherein the distance is determined utilizing the predetermined angle.

18. The system of claim 17, wherein the downhole tool is disposed in a wireline tool.

19. The system of claim 17, wherein the downhole tool is disposed in a drillstring tool.

* * * * *